United States Patent [19]

Schulman et al.

[11] Patent Number: 5,193,540
[45] Date of Patent: Mar. 16, 1993

[54] STRUCTURE AND METHOD OF MANUFACTURE OF AN IMPLANTABLE MICROSTIMULATOR

[75] Inventors: Joseph H. Schulman, Santa Clarita, Calif.; Gerald E. Loeb, Kingston, Canada; John C. Gord, Venice; Primoz Strojnik, Sylmar, all of Calif.

[73] Assignee: Alfred E. Mann Foundation for Scientific Research, Sylmar, Calif.

[21] Appl. No.: 812,051

[22] Filed: Dec. 18, 1991

[51] Int. Cl.$^5$ .............................................. A61N 1/36
[52] U.S. Cl. ............................................... 128/419 R
[58] Field of Search ........... 128/419 C, 419 E, 419 F, 128/419 R, 420 R, 421, 422, 423 R

[56] References Cited

U.S. PATENT DOCUMENTS

| | | | |
|---|---|---|---|
| 3,357,434 | 12/1967 | Abell | 128/419 E |
| 3,646,940 | 3/1972 | Timm et al. | 128/427 |
| 3,667,477 | 6/1972 | Susset et al. | 128/419 E |
| 3,727,616 | 4/1973 | Lenzkes | 128/419 E |
| 3,842,841 | 10/1974 | Brighton et al. | 128/419 F |
| 3,870,051 | 3/1975 | Brindley | 128/419 E |
| 4,006,748 | 2/1977 | Schulman | 128/419 P |
| 4,313,438 | 2/1982 | Greatbatch | 128/419 F |
| 4,333,072 | 6/1982 | Beigel | 340/825.54 |
| 4,333,469 | 6/1982 | Jeffcoat et al. | 128/419 F |
| 4,357,497 | 11/1982 | Hochmair et al. | 128/420.6 |
| 4,440,178 | 4/1984 | Bussard et al. | 128/784 |
| 4,494,545 | 1/1985 | Slocum et al. | 128/419 P |
| 4,524,774 | 6/1985 | Hildebrandt | 128/421 |
| 4,549,546 | 10/1985 | Kelly et al. | 128/419 F |
| 4,611,597 | 9/1986 | Kraus | 128/419 F |
| 4,628,933 | 12/1986 | Michelson | 128/419 R |
| 4,654,880 | 3/1987 | Sontag | 128/420.6 |
| 4,665,896 | 5/1987 | LaForge et al. | 128/419 F |
| 4,679,560 | 7/1987 | Galbraith | 128/419 R |
| 4,739,764 | 4/1988 | Lue et al. | 128/419 R |
| 4,763,656 | 8/1988 | Nauman | 128/421 |
| 4,785,827 | 11/1988 | Fischer | 128/420 |
| 4,934,368 | 6/1990 | Lynch | 128/419 R |
| 4,991,582 | 2/1991 | Byers et al. | 128/419 R |
| 5,094,242 | 3/1992 | Gleason et al. | 128/422 |
| 5,105,811 | 4/1992 | Kuzma | 128/420.6 |

OTHER PUBLICATIONS

Kazimierczok et al, "IEEE Transactions on Circuits and Systems", vol. Cas 34, No. 2, Feb. 1987 pp. 149–158.
Rose et al, "Journal of Neuroscience Methods", vol. 12, 1985, pp. 181–193.
Unknown Author, "CRC Critical Review in Bioengineering" Sep. 1981, pp. 77–79.
Specification Sheet Identification Devices, Inc.
Htderks, "IEEE Transactions on Biomedical Engineering", vol. 35, No. 5, May 1988.
Guyton et al, "Medical & Biological Engineering", Sep. 1974, pp. 613–619.
Hildebrandt et al, "Proc. 7th International Symposium on External Control of Human Extremities", Yugoslavis 7-12 Sep. 1981, pp. 2–15.
Becker "Bulletin of the N.Y. Academy of Sciences", vol. 48, No. 4, May 1972, pp. 627–641.
Robblee et al, "Journal of Electrochemical Society" vol. 130, No. 3, Mar. 1983, pp. 731–733.

*Primary Examiner*—William E. Kamm
*Attorney, Agent, or Firm*—L. Lee Humphries

[57] ABSTRACT

An implantable microstimulator has a structure which is manufactured to be substantially encapsulated within a hermetically-sealed housing inert to body fluids, and of a size and shape capable of implantation in a living body, by expulsion through a hypodermic needle. The internal structure of the microstimulator comprises a coil adapted to function as the secondary winding of a transformer and receive power and control information. Circuit means, including control electronics, a capacitor and electrodes are provided. The electrodes, which may be made one of iridium and the other of tantalum and placed on opposite ends of the microstimulator, or alternatively, an iridium electrode at each end of the microstimulator, are at least partially exposed and provide electrical, stimulating pulses to the body.

45 Claims, 6 Drawing Sheets

STRUCTURE AND METHOD OF MANUFACTURE OF AN IMPLANTABLE MICROSTIMULATOR

This invention was made with Government support under Contract No. NO1-NS-9-2327, awarded by the National Institutes of Health. The Government has certain rights in this invention.

This invention relates to the structure and method of manufacture of a microstimulator for implantation in a living body, in the immediate vicinity of tissue, fluids or other body cells which are desired to be electrically stimulated. It is of a size and shape capable of implantation by expulsion through the lumen of a hypodermic needle.

The microstimulator is substantially encapsulated within a hermetically-sealed housing which is inert to body fluids and provides exposed electrodes for electrically stimulating the desired body cells, whether muscle, nerve, receptor, gland or other area or organ of the body.

This application relates to two other patent applications, one filed on Dec. 18, 1991, entitled Implantable Microstimulator, Ser. No. 07/812,136 and having the same inventors as herein and the other filed on Dec. 12, 1991, entitled Implantable Device Having an Electrolytic Storage Electrode, Ser. No. 07/806,584, invented by one of the inventors hereof.

BACKGROUND

Neurological disorders are often caused by neural impulses failing to reach their natural destination in otherwise functional body systems. Local nerves and muscles may function, but, for various reasons, injury, stroke, or other cause, the stimulating nerve signals do not reach their natural destination. For example, paraplegics and quadraplegics have intact nerves and muscles and only lack the brain to nerve link, which stimulates the muscles into action.

Prosthetic devices have been used for some time to provide electrical stimulation to excite muscle, nerve or other cells. Such devices have ranged in size and complexity from large, bulky systems feeding electrical pulses by conductors passing through the skin, to small, implanted stimulators which are controlled through telemetry signals, such as are discussed in U.S. Pat. No. 4,524,774, Apparatus and Method for the Stimulation of a Human Muscle, invented by Jurges Hildebrandt, issued Jun. 25, 1985. Other devices have comprised a centrally-implanted stimulator package sending stimulation signals to a multitude of distant target sites.

Complications, including the possibility of infection, arise in the use of stimulators which have conductors extending through the skin. On the other hand, in the use of implanted stimulators, difficulties arise in providing suitable, operable stimulators which are small in size and have the capability to receive and store sufficient energy and control information to satisfactorily operate them without direct connection.

The device of the invention uses a source of electrical energy outside the skin, modulated by desired control information, to selectively control and drive numerous, small stimulators disposed at various locations within the body. Thus, for example, a desired, progressive muscular stimulation may be achieved through the successive or simultaneous stimulation of numerous stimulators, directed by a single source of information and energy outside the body.

The construction of a microstimulator presents problems of its own, which are not encountered in the construction of larger-sized biomedical appliances. The extremely small size involves problems and solutions of a different nature than are ordinarily involved. The appropriate design of a suitable, small stimulator, a microstimulator, which can be easily implanted, such as by expulsion through a hypodermic needle, is difficult to achieve. Notwithstanding the small size and required shape, the microstimulator structure must contain means for receiving and storing sufficient energy to provide the desired stimulating pulses, as well as electronics which provides control of the characteristics desired of the stimulating pulse.

SUMMARY OF THE INVENTION

This invention teaches an implantable, microstimulator useful in a wide variety of applications. Others have proposed microstimulators and have suggested constructing them, but none have taught all the elements set forth herein for successful construction and operation of the microstimulator.

The device of the invention is a very small stimulator, a microstimulator, which can be easily implanted, such as by expulsion through a hypodermic needle and which microstimulator provides electrical stimulation pulses of desired characteristics. Stimulation pulses are delivered to the body through electrodes exposed on the outer surface of the microstimulator.

Within the microstimulator, an induction coil receives energy from outside the body and a capacitor is used to store electrical energy which is controllably released to the microstimulator's exposed electrodes. The body fluids and tissue between the exposed electrodes provide the electrical path for the stimulating pulse. The capacitor is controllably recharged, using the same or different exposed electrodes. In this manner, a "charge balancing" is achieved, that is, a balancing of current flow through the body tissue in both directions to prevent damage to the tissue which results from continued, preponderance of current flow in one direction.

The induction coil which receives energy and control information from a modulated, alternating magnetic field acts as a secondary winding of a transformer and receives the energy which is rectified and stored on a capacitor. The modulation is detected and decoded to provide the desired control information.

Of great importance in the microstimulator are the structures of the electrodes. They must meet the requirements of inertness to body fluids, be hermetically-sealable to the housing, and formable to the desired size and shape. They must meet the operating requirements of the electrical circuit and not deteriorate in cathodic and anodic operation, as the stimulating pulses are generated and as the recharging of the system occurs.

It is, therefore, an object of this invention to provide a microstimulator that is inert and hermetically-sealed, and of a size and shape capable of implantation by expulsion through a hypodermic needle.

Another object of this invention to provide a microstimulator structure housing a coil adapted to receive an alternating magnetic field to provide a source of power for the microstimulator.

It is another object of this invention to provide a microstimulator comprising capacitor means for storage of electrical energy.

Still another object of this invention is to provide a microstimulator which contains an assembly of induction coil and electronics to receive and detect a signal modulating an alternating field and to control a stimulating pulse in accordance with such modulation.

A still further object of this invention is to provide a microstimulator having at least partially-exposed electrodes.

Another object of this invention is to provide a method of manufacture of a microstimulator.

A further object of this invention is to provide a method of manufacture of the electrodes of a microstimulator.

A final object of this invention is to provide a method of sealing said microstimulator to its exposed electrodes.

DESCRIPTION OF THE DRAWINGS

Further objects and features will be apparent from the following description and drawings in which.

DETAILED DESCRIPTION OF THE DRAWINGS

The microstimulator of the invention is on the order of 2 mm in diameter and 10 mm long. Because of such diminutive character, it is readily implanted in a living person or animal through the lumen of a hypodermic needle. But, because of its small size, it has been difficult to establish the parameters of such a microstimulator in order to obtain the desired operating characteristics. The following description sets forth suitable, working parameters for constructing such a microstimulator.

Figure 1:
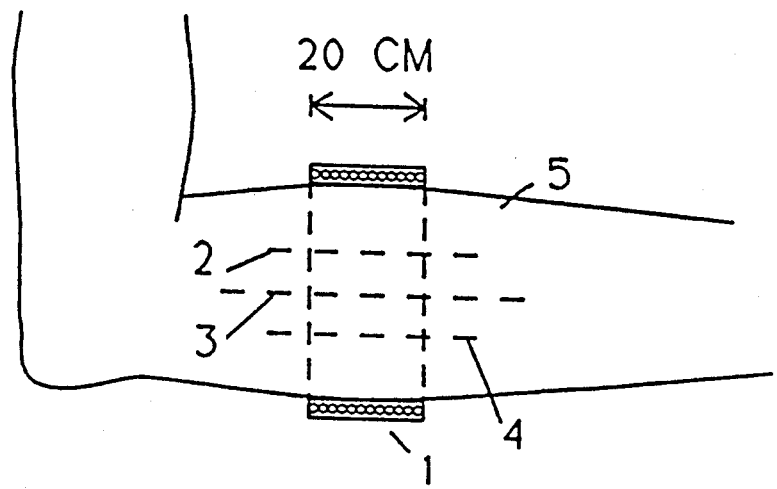
FIG. 1 is an overall view of the device of the invention as applied to an arm, showing the primary coil in cross-section and a representation of a number of microstimulators implanted in the arm.

FIG. 1 shows, figuratively, how an external, primary coil 1, which produces an alternating magnetic field, at a frequency, say, of 2 mHz, is disposed with respect to a number of microstimulators such as 2, 3, and 4, implanted, say, in an arm 5. The microstimulators, of course, may be planted in or near any part of the body, in the brain, a muscle, nerve, organ or other body area.

The system operates as an air-gap transformer in which coil 1 is the primary winding, exterior to the body, and the microstimulators 2, 3 and 4 each have coils within them which act as secondary windings of the transformer.

Coil 1 may, for example, be 12 to 20 turns of #200/38 Litz wire, and wound 20 cm long and 9 cm in diameter for operation with, for example, 256 microstimulators implanted in an arm. Each microstimulator has its own identifying address and, therefore, is individually addressable. The wire, for example, may be 50 or 51 gauge copper wire (diameter of 0.001 inch) insulated with less than a 0.4 mil thick polyimide insulation.

Alternatively, coil 1 may be a pancake type coil or a saddle-type coil and disposed on the surface of the skin and not necessarily entirely encompass a limb or other body part. It may not, in such case, be as efficient in transferring energy to the microstimulators.

The means of driving coil 1 is, preferably, a class E driver, but may be any one of those suitable drivers known to those skilled in the art. Class E drivers are well-known in the art and an analysis of them may be found in an article entitled, *"Exact Analysis of Class E tuned Power Amplifier at any Q and Switch Duty Cycle,"* Kazimierczuk and Puczko, IEEE Transactions on Circuits and Systems, Vol. CAS-34, No. 2 February, 1987, pp. 149-159. Numerous additional references are therein cited. Inductive transdermal links are further disclosed and discussed in U.S. Pat. No. 4,679,560, for Wide Band Inductive Transdermal Power and Data Link, inventor, Douglas C. Galbraith and in *"RF Powering of Millimeter- and Submillimeter-Sized Neural Prosthetic Implants,"*, William J. Heetderks, IEEE Transactions on Biomedical Engineering, Vol. 35, No. 5, May 1988.

Figure 2:
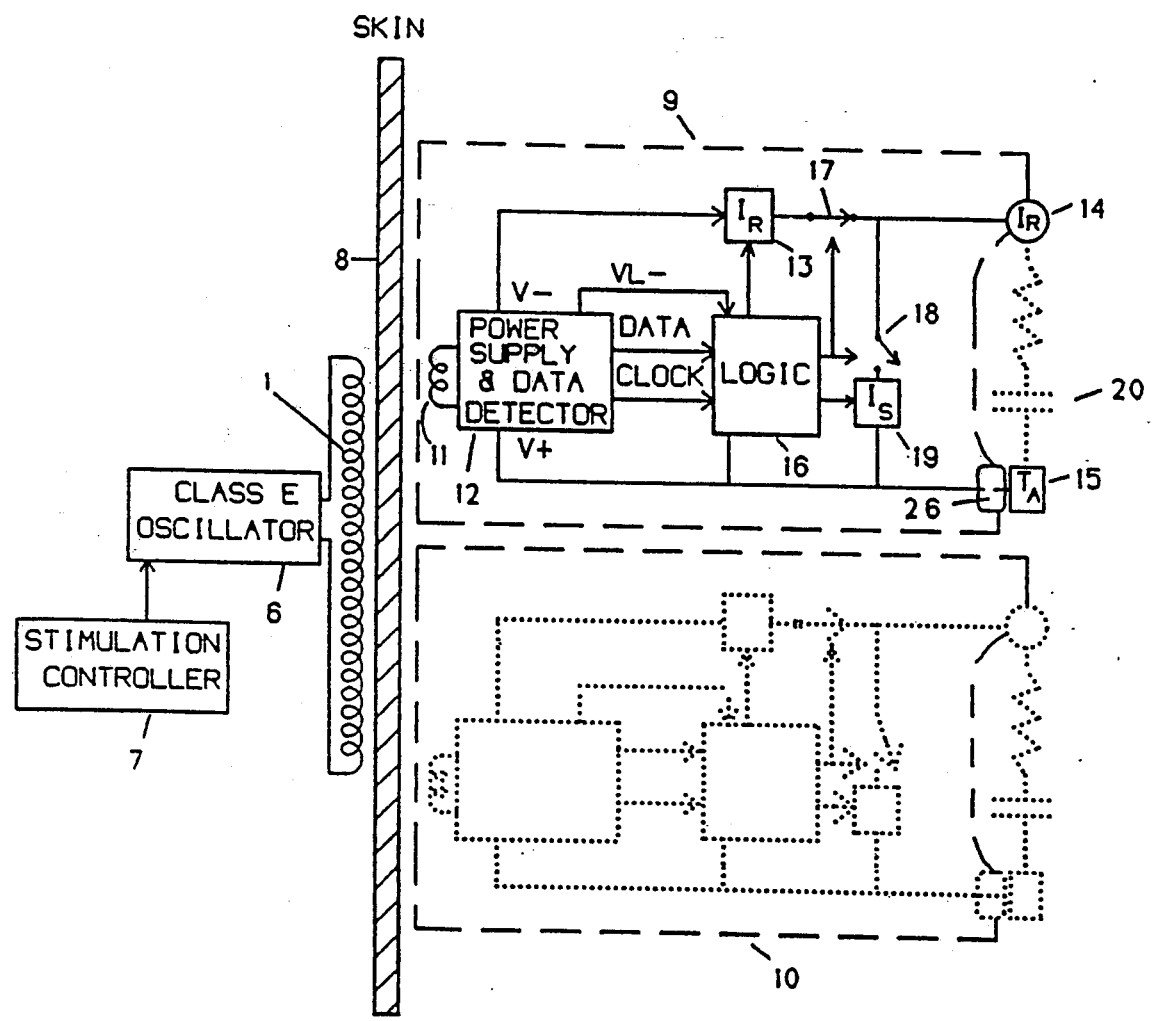
FIG. 2 is block diagram illustrating the transcutaneous transmission of power and information to implanted microstimulators.

FIG. 2 is a block diagram illustrating the transcutaneous transmission of power and information to implanted microstimulators by a class E driver. It shows a modulated, power source on the left, the skin and two implanted microstimulators on the right. Coil 1 is driven by a modulated oscillator 6 which in turn is driven by a stimulation controller 7. Underneath (shown to the right of) skin 8 are implanted microstimulators such as 9 and 10. Microstimulator 9 is shown in greater detail. Secondary coil 11, within microstimulator 9 receives energy and control information from the modulated, alternating magnetic field provided by coil 1 and passes such energy and information to power supply and data detector 12 which, in turn, provides power through an electrode recharge current controller 13 to stimulating electrodes 14 and 15.

FIG. 2 shows secondary coil 11 at or near the surface of the skin. Such is for illustration only. The microstimulator may be much deeper, if desired, or at any location within the arm, along the length of the transmitting coil 1, FIG. 1 and, even, for some distance beyond the ends of the coil 1. In one experimental determination, it was found that the microstimulators may lie as far as about 5 cm. outside the volume encompassed by coil 1.

The power supply portion of 12 provides voltage at two levels, for example, approximately −7 to −15 volts, for providing stimulating pulse energy storage and −2 to −4 volts for power for digital logic 16. Data detector 12 also provides clock and digital data information to logic 16 which decodes the control information contained within the modulated, alternating magnet field. Such decoded information is used by the logic 16 to control switch 17 which controls the charge stored on the capacitor 20, between electrodes 14 and 15. Logic 16, which is preferably high speed, low current, silicon gate CMOS, also controls switch 18, (which may be a transistor), which controls the stimulating pulse current (which is a discharge of the stored charge between electrodes 14 and 15) which flows between electrodes 14 and 15. Logic 16 also controls current amplitude buffer 19. This controls the amount of current allowed to flow in each stimulating pulse.

Figure 3:
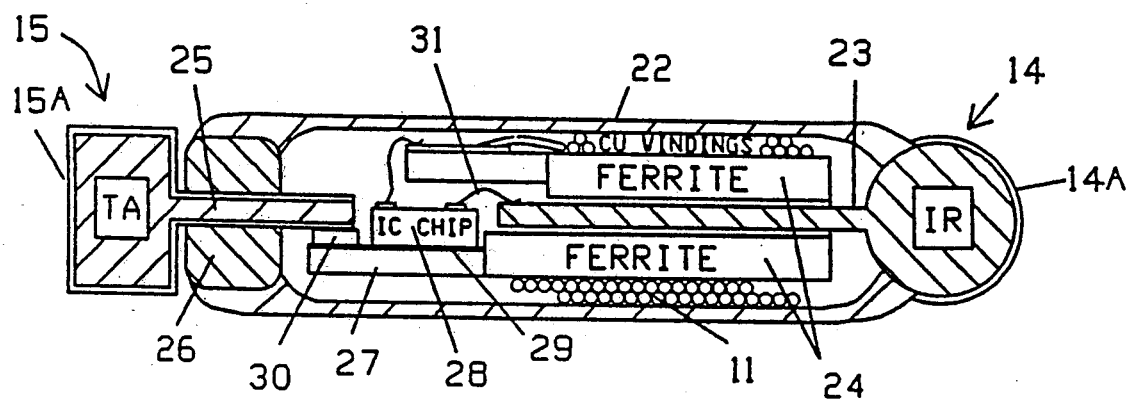
FIG. 3 is a cross-section side view of a microstimulator.

In FIG. 3, electrode 14, a preferred embodiment, comprises an iridium ball having a stem extending into the microstimulator. The iridium ball and stem are formed by melting a fine iridium wire such that it forms a ball at the end of the wire. A substantial portion of the iridium ball is exposed outside the stimulator and is activated, as described hereinafter.

In FIG. 3, electrode 15, in the preferred embodiment, is placed at the opposite end of the microstimulator from electrode 14, and is comprised of anodized, sintered tantalum, and has a stem 25 extending into the microstimulator. A substantial portion of the tantalum electrode is also exposed outside the stimulator.

Electrode 15 is constructed of powdered tantalum metal molded and sintered into a pellet on the end of a 0.25 mm diameter wire, tantalum stem. It is then anodized, to form a thin anodized layer 15A, and the tantalum stem is threaded through a glass bead of N51A soda-lime glass and the portion of the stem protruding inside the glass bead is gold plate (plating not shown). The anodization may be left until after the housing is sealed to the glass bead because the heat may affect the anodization. The glass bead is preferably of the size of the tantalum pellet, approximately 0.060" in diameter and 0.042" in width. The entire length of the tantalum electrode is approximately 0.110". The porous nature of the pellet allows intimate relationship with the body fluids, but is of sufficiently small cellular structure that fibrous growth does not occur within the cells. The pellet is the outer, exposed portion of the electrode and is formed as a cylindrical section approximately less than 2 mm long and 2 mm in diameter, (approximately 6 or 7 mm$^3$). The outer exposed pellet comprises, by its porous structure and anodized layer, an electrolytic capacitor, shown as capacitor 20, FIG. 2, with resistance 21 illustrating the resistance of the path through the body, approximately 300 ohms, between the electrodes. the electrolytic capacitance of capacitor 20, provided by tantalum electrode 15 and iridium counterelectrode 14, can be significant, being on the order of 2 to 30 microfarads. For greater capacitance, the outer cylindrical section of tantalum electrode 15 can be larger, but it is expected that sufficient capacitance can be achieved by a volume of 7 mm$^3$. It has been found by others that anodized tantalum has a very low DC leakage level when biased up to 80% of the anodization voltage and tends to self-heal in body fluids. In other embodiments, a discrete capacitor within the microstimulator, in series circuit with electrode 15 may provide such capacitance, as illustrated by capacitor 50 in FIG. 9. Such discrete capacitor, constructed in accordance with well-known art, would occupy a substantial amount of space within the microstimulator in order to achieve the same capacitance as the sintered electrode.

Thus, all of the elements to receive and store modulated, electrical energy and to decode and use the modulating information to cause stimulating pulses, is provided by the microstimulator. Such elements are all within the microstimulator except for the exposed electrodes and, in the preferred embodiment, the storage capacitor for storing the energy for the stimulating pulses. Such a storage capacitor, which is an electrolytic capacitor, is provided by one of the exposed electrodes, porous tantalum electrode 15, immersed in body fluids, together with its iridium counterelectrode 14, FIG. 2.

A further embodiment would be one in which one or both of said electrodes are formed in the shape of a single or plural nerve cuffs, as taught in U.S. Pat. No. 4,934,368, Multi-Electrode Neurological Stimulation Apparatus, in order to innervate nerves, as opposed to localized muscles. For example, platinum wires extending out of each end of the microstimulator could then be connected to the appropriate nerve cuff. The stimulating pulse would not need to be as large as those described herein. Although the size is miniature, in the nerve cuff application, the device would likely be surgically implanted.

FIG. 3 is a cross-section side view of a micro stimulator. A housing 22 is, in a preferred embodiment, glass capillary tubing approximately 10 mm long and having an outer diameter of approximately 2 mm. Such glass capillary tubing is preferably a biocompatible, lime glass or borosilicate glass and is commonly available from or through glass fabrication houses such as Kimbel Glass or Corning Glass. Additionally, the housing may be a ceramic, cast or molded epoxy or silicon rubber, or other material which is hermetically-sealable, inert and suitable for implantation.

At one end, the glass is hermetically-sealed to an electrode 14, which electrode comprises an iridium ball having an iridium stem 23 extending into the microstimulator. The iridium ball and stem are formed by melting a 0.006" or 0.010" iridium wire such that it forms a ball at the end of the wire. The wire may be lowered vertically into the tip of an oxy-acetylene flame and the iridium will melt and retract to form a ball on the end of the stem. Too large a ball will fall off. Care is taken during rapid cooling to center the ball on the stem. The other end of the stem may be cold-formed to provide a flat for bonding a wire thereto, to make electrical connection to the electrode.

It is important to select a glass which is stable in body fluids and which matches pretty well the coefficient of thermal expansion of the tantalum and iridium because of the heating operations involved in fusing the electrodes to the glass housing. Glass capillary tubing, N51A, has a coefficient of thermal expansion similar to tantalum and iridium and thus may be sealed thereto. The tubing is cut off square about 2 mm beyond the end of ferrite core 24.

In operation, the tantalum electrode may be charged to +15 volts, with the iridium as the counter electrode. Upon discharge, or partial discharge of the charge, due to a stimulating pulse, the tantalum may drop substantially in voltage, say, to 8 volts, but the iridium remains at approximately −0.4 volts. The combination of tantalum and iridium allow the tantalum to be charged to a high voltage, necessary for the stimulating pulse.

At the other end of the microstimulator from iridium electrode 14, is tantalum electrode 15, which is comprised of anodized, sintered (porous) tantalum and has a stem 25, preferably of solid tantalum wire, extending into the microstimulator. Before anodizing, the tantalum electrode, is cleaned by stripping the oxide from it by a 20 second bath in 40% HF acid. The stem is given a diamond polish, where the glass bead 26 is to be sealed, to remove the scratches and nicks. The electrode may then be anodized (but anodization is preferably left until after fusing the electrode and glass bead to the housing) and the glass bead 26 is threaded onto the stem 25 and fused thereto. The stem, inwardly of the glass bead, is then gold-plated. Anodization is accomplished by a constant current of 100 microamperes through the anodizing solution (0.1 vol % $H_3PO_4$ at 84 degrees C.). Anodizing for 1 hour to +10 VDC will give approximately 10 microfarads capacitance. Anodizing longer to +20 V DC will give approximately 6 microfarads capacitance. Tantalum also has a coefficient of thermal expansion compatible with N51A glass, but porous tantalum will ignite and burn if placed in a flame, such as when seeking to seal stem 25 to the glass housing 22.

When the glass bead 26 is being fused to the tantalum stem 25 and when the glass bead 26 is being fused to the housing 22, a heat sink fixture, which may be a nose cone of tantalum, is slipped over the porous electrode 15 to draw heat away from the electrode and keep the tantalum stem 25 from reaching the melting temperature required in order to fuse the glass bead to the stem and the glass bead to the housing. Also, a two-piece heat shield collar, or collet, is placed between the electrode 15 and the glass bead 74, not quite touching the tantalum electrode. Such collar can help to maintain a 0.010" spacing between the end of the microstimulator housing and the electrode 15. Such gap functions as an anchor, allowing tissue to fill in and holds the microstimulator in place.

Anodization of the tantalum would then be done if it has been left until after the fusing of the glass bead to the housing.

A suitable fixture for accomplishing the fusing of the housing to the electrodes is an assembly of three simultaneously-adjustable microtorches disposed around a rotatable chuck. Such microtorches may use propane (such as from tanks used for household plumbing) mixed with oxygen and fed through a 22 gauge (0.016" I.D.) needle. The chuck is tapered to reduce its heat sinking capability and allow the glass housing to heat better.

The glass bead 26 is placed on the stem 25 of the tantalum electrode 15 and fused thereto. The chuck for holding the tantalum electrode 15 should also be of tantalum to avoid scratching and embedding of foreign metal particles in the electrode. When the electrodes are to be fused to the housing, after the coil and electronics are inserted therein, the housing is inserted in a chuck and is held vertically downward to avoid distortion due to gravity.

There are various methods of assembly. In the preferred method, the entire internal assembly is put together and inserted into the housing from one end of the housing or the other. Prior to inserting the assembly, the glass bead 26 is threaded onto the anodized tantalum stem 25 and fused thereto. The inner end of the tantalum stem is gold-plated. A metallized film 29 is deposited on the bottom ferrite shelf. The IC electronics chip 28 is adhered to the metallic film 29 on ferrite shelf 27 by silver epoxy, silver solder, an indium-based solder, or other suitable conductive adhesive. Two metallized pads 32 and 33 are created on the top half of the ferrite core. A polyimide, solder resist line, or barrier 38, is added. The tantalum stem 25 is resistance welded or soldered to the weld shim 30.

Another method of connection of the tantalum stem 25 to electronic chip 28, rather than by means of metallized film 29 and the substrate of the electronic chip 28, is to replace the shim 30 and the metallized film 29, with a small metallized pad disposed on the ferrite shelf 27 to which both stem 25 and electronic chip 28 are connected by flying wire bonds, or other means.

One side of the iridium ball is remelted, prior to its assembly, to present a very smooth surface for fusing to the housing 22. The iridium electrode is cleaned by reduction in a saline solution with 3 to 6 volts applied. The iridium stem is inserted through the ferrite channel of the bottom half of the ferrite core and by electrical conductor 31, is connected electrically to the electronic chip 28. A silver epoxy may be used to reinforce such electrical connection. Additional silver epoxy may be used to fill up the channel and provide a heat sink for the iridium electrode.

The top half of the ferrite core is placed over the bottom half of the ferrite core and one end of the coil wire is soldered to a metallized pad, 32, for example, and the coil is wound on the ferrite and the other end is soldered to the other metallized pad 33. Gold wires are bonded between the metallized pads 32 and 33 and the electronic chip pads 36 and 37. A junction coat is applied.

The iridium ball and its stem, along with the entire inner assembly, are inserted into one end of the glass capillary tube. The glass is sealed to the smooth surface of the iridium ball, by bringing the glass and iridium ball into an oxy-acetylene flame and rotating them within the flame. Ball diameters were tested from 0.038" (0.97 mm) to 0.050" (1.25 mm), just slightly smaller than the inner diameter of the 2 mm D glass tubing, and it was found that the larger ball sealed quicker and were easier to keep centered and gave a longer seal path. The preferred diameter is 0.060". The larger ball also provides a larger exposed electrode surface, outside the glass housing. The sealing operation may be viewed under a microscope. It will be noted that the glass will shrink backward during melting, but the portion of exposed ball ($\frac{1}{4}$, $\frac{1}{2}$ or $\frac{3}{4}$) before sealing is proportional to the exposed portion after sealing. In FIG. 3 approximately 60% of the iridium ball is shown exposed outside the microstimulator.

The glass bead 26 on the tantalum stem 25 on the other end of the microstimulator is flame-sealed, or fused, to the glass tubing, housing 22.

The outwardly exposed portion of the tantalum electrode 15 may then be anodized, as explained previously.

The exposed portion of the iridium electrode 14 is activated after the sealing of the iridium electrode 14 to the glass tubing 22. This is done by immersing the exposed portion of the iridium electrode 14 in a phosphate-buffered saline solution and touching its outside surface with a whisker probe (0.003") of iridium wire, cycling for 10 to 30 minutes at 0.5 volts per second between plus and minus 0.8 volts (relative to the standard Calomel electrode), just below the voltage at which electrolysis occurs. The cyclic voltammetry builds up an electrically conductive layer of iridium hydrous oxide, layer 14A, that is capable of being cycled reversibly between the +3 and +4 valence states, thereby transforming electron motion in the underlying metal into ion fluxes in the surrounding solution without inducing irreversible electrolysis of the water or metal. The interfacial impedance tends to be very low, also, the voltage which is necessary to obtain stimulation is reduced.

Activation creates a hydroxide or oxide layer on the surface of the iridium. Such activation layer, in iridium, provides a substantial amount of capacitance.

It has been determined that the metallized pads 32 and 33 on the top half of the ferrite core 24 may be made of indium solder and no barrier 38 is then required. Metallized pads 32 and 33 may be created of palladium, silver, indium, or solder, or mixtures thereof. The flying, gold, bond wires may be attached directly from such pads to the electronic chip 28.

Other means may used to make the electrical connections within the microstimulator. For example, a polyimide cap (Kapton) may be used. It is placed on the electronic chip 28 and provides solder pads on the top for connecting to the electrodes and the coil and on the bottom for connecting to the electronics chip 29. Thruhole connections, in the cap itself, make connections between the top and bottom of the cap.

In a second method, the assembly (without the tantalum electrode, including the wire) is inserted in the housing. The iridium stem 23 has already been inserted into the core and electrically connected to the electronic control circuitry 28. Weld shim 30, FIGS. 3 and 4, has solder, conductive epoxy or other flux disposed on it. The bottom end of the housing is melted back until it is curved inwardly to form a small opening. The stem 25 of the tantalum electrode has been fed through the glass bead 26 and fused thereto. The tantalum electrode 15 and the fused glass bead 26 are inserted into the bottom end of the housing for fusing of the glass bead to the housing, using the microtorches. The heat of fusing the glass bead to the housing melts the flux on the weld shim 30 and tantalum stem 25 becomes electrically fused to the weld shim. In order to construct the embodiment shown in FIG. 5, in which there is no weld shim, the tantalum electrode stem 25 is finally connected directly to the electronic chip 28 by means of conductive epoxy 39. If desired, it may be caused to fuse to the tantalum stem 25 and the electronic chip 28 by the heat fusing glass bead 26 to housing 22. Iridium electrode 14 may be hermetically sealed to the housing 22 before or after the glass bead 26 is hermetically sealed to the housing 22.

In a third method of assembly, the assembly of the tantalum electrode 15, the electronic chip 28, the coil 11 and the ferrite core 24, is inserted into the housing. Then the iridium stem 22 is inserted into the housing and through the channel in the ferrite core, to a conductive epoxy or other conductive material which may serve to connect it to the electronic chip 28 or to a conductor connecting thereto. The ends of the housing are hermetically sealed to the electrodes 14 and 15 as previously described.

The epoxy disposed within the channel, around iridium stem 23, effectively serves to provide a heat sink for the iridium electrode into the ferrite core.

A bottom chuck holds heat sink means which can be used to shield the outer end portion of the tantalum electrode from the direct flame.

The tantalum and iridium wire, used in the microstimulator, will be found to have irregularities comprising voids, linear scratches and furrows, from the drawing process. Such irregularities may result in leaks when fused to the glass. Cleaning, polishing, annealing or other processes for smoothing such wires will improve the success rate of hermetic sealing.

The problem of irregularities as to the iridium electrode 14 was overcome by reheating the part of the ball to be fused, cleaning the ball as explained previously, and fusing the housing to the back of the iridium ball, which had been formed of the iridium wire.

To achieve a satisfactory success rate for bonding tantalum to glass a cleaning process was used for the tantalum wire which comprised abrading by hand with 600 grit (30 micrometer) SiO paper, then with 6 micrometer diamond paste using the buffing wheel of a Dremel tool, followed by an ultrasonic cleaning procedure of 1 minute each in trichloroethylene, methanol, detergent and distilled water, rinsed in distilled water, methanol, and freon TF.

Testing for hermeticity may be done by helium, but the helium may leak out before the test can be made. Finished devices are best tested by soaking in a dye solution and rejecting those parts that exhibit streams of bubbles or internal dye droplets.

Figure 4:
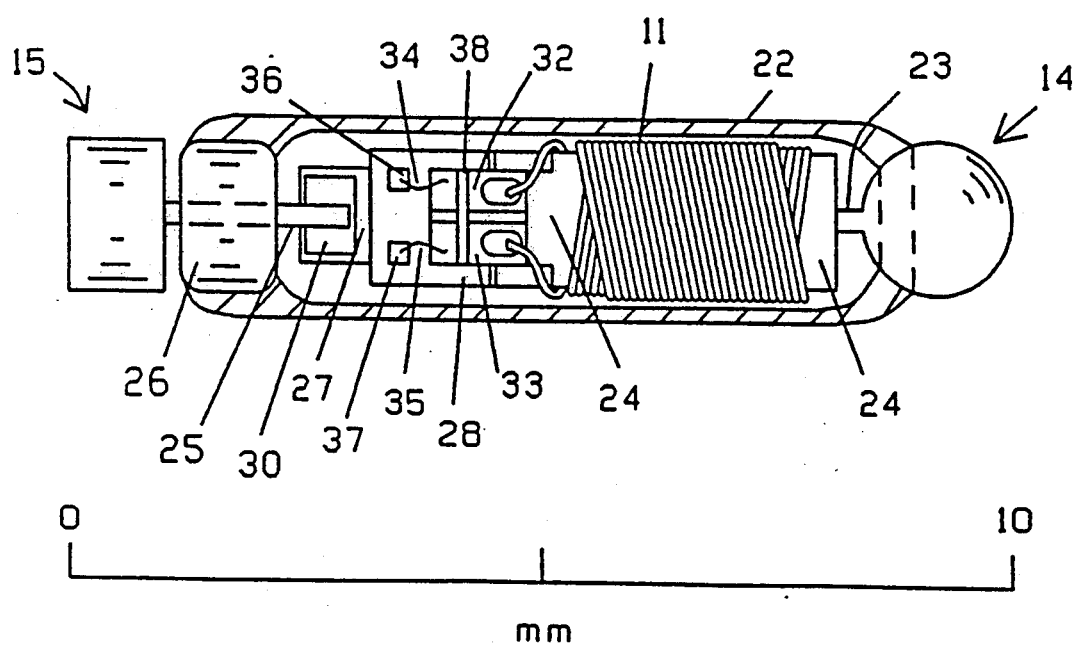
FIG. 4 is a top view of a microstimulator with the housing in cross-section.

The embodiment shown in FIGS. 3 and 4 illustrates the coil 11 which, depending on the particular application, has approximately 200 turns or more, to provide the necessary induction for the secondary of the transformer. In one preferred embodiment, approximately 250 turns of 51 AWG, (0.00102" diameter or smaller) insulated, copper wire is wound in two layers on the ferrite core 24, having a diameter of approximately 0.050". Such construction will by its own distributed capacitance be resonant at approximately 2 mHz. Although an air core and other cores of high-permeability and low losses could be made to work, a ferrite core is preferred. A particular core material which was used and found satisfactory was a low conductivity, high permeability, nickel-zinc ferrite stock, having a permeability of 800. It was formed by cutting and grinding two half cylinders, to the shape shown in FIGS. 3 and 4, with a groove in each, to form a hollow core when the two half cylinders were placed together.

The bottom half of ferrite core 24 is longer than the top half and provides a shelf 27 on which to mount the electronic chip 28 (a custom, integrated, microcircuit chip) for the microstimulator. It is noted that the top half of ferrite core 24 extends over electronic chip 28 and on the top surface of ferrite core 24 are disposed the metallic pads 32 and 33, FIG. 4 to which are connected the ends of the coil. In a preferred embodiment, electronic chip 28 is a double-poly P-well CMOS (3 micron) process so that the substrate is at the V+ supply rail to which the tantalum stem of electrode 15 is connected. It is noted that both ends of the coil 11 are electrically connected to provide input to the electronic chip 28, providing the energy (for powering the microstimulator) and the modulation (control) information to such electronic chip 28. The chip dimensions may be approximately 0.050" with aluminum pads approximately 0.006" square for conventional gold-wire ball-bonding.

One output of electronic chip 28 is to the tantalum electrode 15, and is shown in FIG. 3 as being through the substrate (base) of the electronic chip 28 to a thick, conductive film 29 which may be plated or adhered to ferrite shelf. Electrical connection between the electronic chip 28 and the film 29 may be accomplished by a silver-filled conductive epoxy or other electrically conductive means. The preferred thick, conductive film is screenable or imageable (by screen printing or photolithography or other imaging method). An alloy of the platinum group and gold (specifically, Pt/Pd/Au) in a fritted paste is preferred. Such is then fired for about 60 minutes, being raised evenly, 50 degrees Centigrade per minute, to approximately 850 to 1050 degrees Centigrade in 30 minutes and cooling at the same rate. Such film shows good weldability and good solderability.

Weld shim 30, which is conductive, is also bonded or otherwise adhered to conductive film 29 and is resistance welded, or otherwise electrically connected to tantalum stem 25. Stem 25 comprises part of tantalum electrode 15 and extends through glass bead 26 to the exposed pellet of tantalum electrode 15.

Electrical connection between the tantalum stem 25 and the electronic chip 28 may also be made by a wire-bond between them or by a flying wire bond from each of them to a small metal pad (not shown) on ferrite shelf 24. Such connection may also be made as described in connection with FIG. 5, hereafter.

The other output of electronic chip 28 is connected to iridium stem 23 by means of wire 31.

The electric stimulation occurs through discharge of electrolytic capacitor 20, FIG. 2 (provided by the porous, exposed end of electrode 15) upon connecting electrodes 14 and 15 together inside the control circuit. The stimulation pulse, of course, passes through the body between electrodes 14 and 15.

FIG. 4 is a top view of a microstimulator with the housing in cross-section. The ends of coil 11 are connected to two metallized pads 32 and 33 (of palladium-silver, for example) plated on ferrite 24, by means of conductive epoxy or soldering. Such pads 32 and 33 are connected by flying, gold wires 34 and 35 which are bonded to aluminized pads 36 and 37 on electronic chip 28 and protected with a junction coat. Barrier 38, which may, for example, be polyimide isolates the conductive epoxy and solder from flowing to undesired areas.

The microstimulator may be filled with a harmless, inert gas which is also compatible with the internal structure of the microstimulator. Prior to fusing of the second electrode to the housing, the inert gas may be introduced into the microstimulator, or the microstimulator may be assembled in an inert gas atmosphere. The inert gas may be 10% helium and 90% argon or krypton or other commonly-used, suitable, biologically-compatible gas. Assembly in a dry, relatively clean atmosphere has been found suitable. All epoxy inside the microstimulator must be allowed to fully cure before sealing, otherwise undesired by-products are generated within the microstimulator as the epoxy cures.

Figure 5:
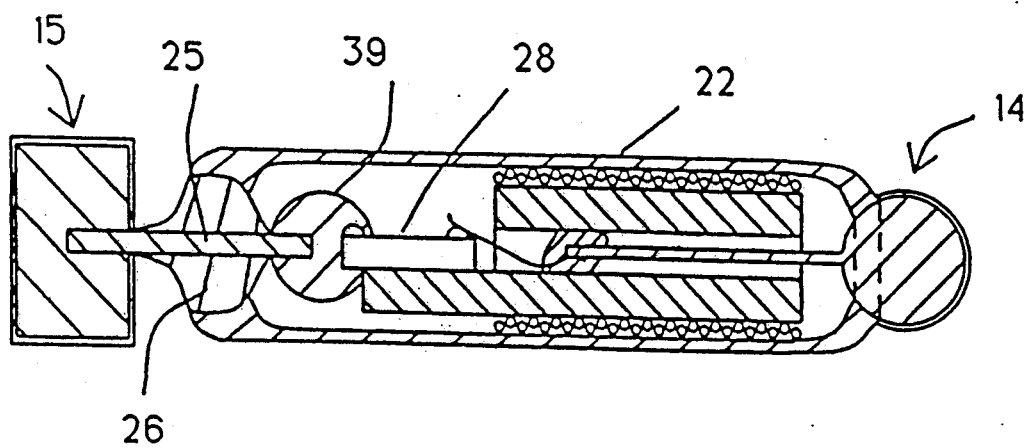
FIG. 5 is a top view of a slightly alternate construction, showing the housing in cross-section and using conductive epoxy, silver solder or other conductive material to make the electrical connection to both electrodes.

FIG. 5 shows an alternate means of connecting the tantalum stem of electrode 15 to electronic chip 28. Conductive epoxy 39 is used to provide an electrical connection between the stem and a metallic pad on the electronic chip 28. This construction would be most adapted to the second method of assembly, mentioned previously, in which the heat of fusing the electrode 15 to the housing 22 provides heat to a flux (the conductive epoxy) to connect stem 25 to the electronic chip 28.

Figure 6:
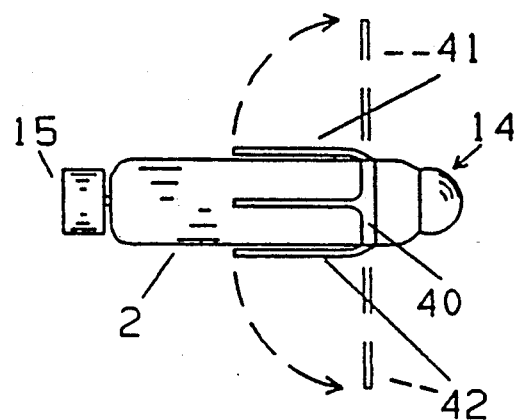
FIG. 6 shows a microstimulator having an anchor skirt.

FIG. 6 shows a microstimulator having an anchor skirt 40 fitted around the waist of microstimulator 2, to provide a means for anchoring the microstimulator within the body. As the microstimulator is released from the hypodermic needle, the arms 41 and 42 (and any other arms) resiliently spring away from the body of the microstimulator to an extended position where they hold the microstimulator against movement within the body. The microstimulator may also be anchored by the spacing of the enlarged end of the electrode 15, a small distance, say, 0.010", away from the end of the microstimulator, as explained previously in connection with the discussion concerning the tantalum electrode.

It is possible to construct the electrodes 14 and 15 in other shapes, sizes and disposition. They may be constructed of platinum or other suitable metal. For example, platinum wire may be used to make electrical connection through the ends of the microstimulator housing to electrodes plated or otherwise attached to the housing, or to electrodes removed from the housing.

Figure 7:
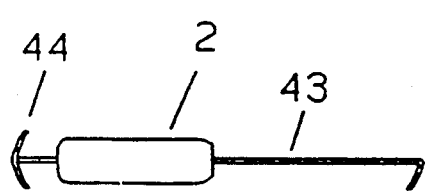
FIG. 7 shows a microstimulator having electrodes with barbs.

FIG. 7 shows a microstimulator 2 having an extended electrode 43 having a barb at its end, to hold the electrode and the microstimulator in place. At the other end of microstimulator 2 is shown a short electrode 44 having two barbs at its outer end. It is to be appreciated that two or more electrodes, such as 43 may extend from one or both ends of the microstimulator.

Figure 8:
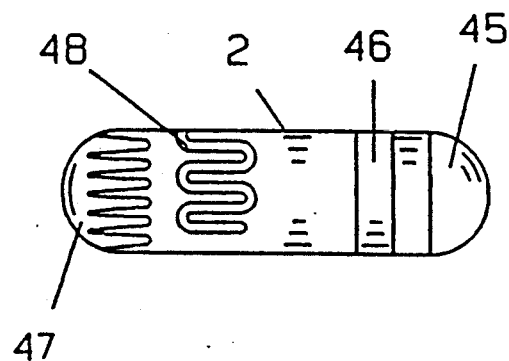
FIG. 8 shows a microstimulator having electrodes attached to the surface of the housing of the stimulator.

FIG. 8 shows a microstimulator having electrodes on the surface of the housing of the stimulator. Electrode 45, for example, may be an adhered film or plated conductor, attached, of course, to a conductor penetrating into the housing of microstimulator 2, as shown by tantalum wire 25 in FIGS. 3 and 4, for example. Iridium, platinum or other metal may also provide such conductor. Metallic band 46 may be electrically connected to electrode 45, or isolated therefrom, having its own connection to the microstimulator. The external electrodes may also take the form shown by comb electrode 47 and serpentine electrode 48. Such structures would serve to reduce heating of the external electrodes in the alternating magnetic field. The comb, serpentine and similar electrodes, on a much larger scale, are disclosed in U.S. Pat. No. 4,006,748, Implantable Unipolar Pacemaker with Improved Outer Electrode Plate, invented by Joseph H. Schulman. Such electrodes may be suitably made in the instant invention by microphotolithographic techniques.

In one embodiment, an iridium ball electrode may be utilized at both ends of the microstimulator. In that event, the body fluids capacitor 20, FIG. 2, would be replaced by a capacitor internal to the microstimulator. This embodiment is more fully discussed in connection with FIG. 10.

Also, in the event the electrolytic tantalum electrode 15 is not used, or, if it is desired to supplement the capacitance provided by such electrode, an additional internal capacitance may be provided. In FIGS. 3 and 4, the weld shim 30 could be replaced by a tantalum sintered slug capacitor which may be purchased. One side of the internal capacitor, as with the weld shim, is connected to the tantalum stem 25 and the other side of the internal capacitor is connected to the metallized film 29, which is further connected to electronic circuitry 29.

The construction details of a successful microstimulator are vital because of the extremely small size. Space is at a premium. In a preferred embodiment, the core 24 provides a coil form, a mount for the electronics chip 28, a mount for the metallized connection pads 32 and 33 and a channel through which one of the electrodes extends.

Figure 9:
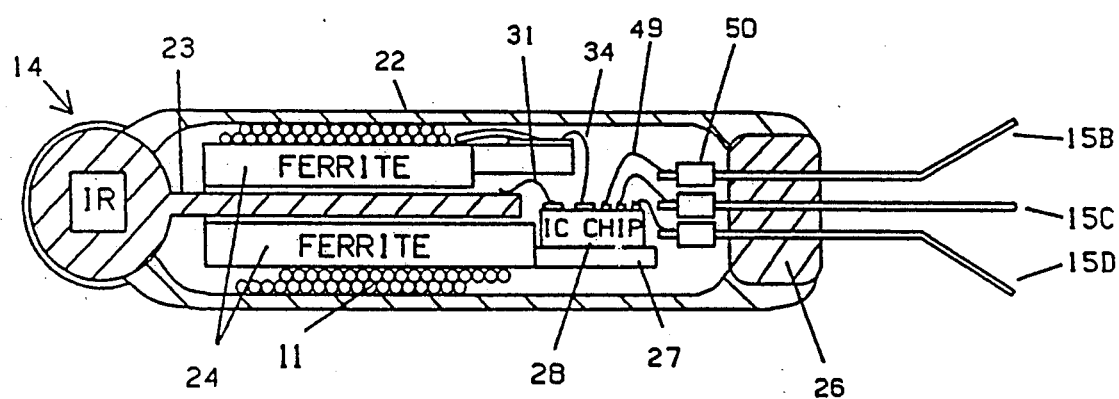
FIG. 9 illustrates a multiple electrodes in one end of the microstimulator and individual, internal storage capacitors.

FIG. 9 illustrates another embodiment of the microstimulator in which multiple electrodes 15B, 15C; and 15D are disposed in one end and an electrode, such as iridium electrode 14 is disposed in the other end. In this embodiment, neither of the electrodes are electrolytic and the storage capacitor means is provided inside the microstimulator. In FIG. 9, electrodes 15B, 15C and 15D pass through individual holes in glass bead 26, are fused thereto, and the glass bead is fused to the housing 22. Individual storage capacitors, such as axial capacitor 50 are connected to each electrode and provide the electrical storage capacitance therefor. Such capacitors, on their inward end, are connected to connection pads on electronic circuitry chip 28. Such capacitors may be electrolytic, axial, tantalum capacitors or other suitable, miniature capacitors which are readily commercially available.

A single capacitor may be used internally, and all electrodes 15B, 15C and 15D may be mutually connected to one side and the other side of such capacitor, such as capacitor 50, may be connected to a pad on the electronic circuitry chip 28, to be controlled thereby. One embodiment uses an iridium electrode at each end of the microstimulator. One of the iridium electrodes is connected to a single, internal capacitor, or multiple capacitors in parallel, such as capacitor 50, whose other end or ends would be connected to the electronic circuitry chip 28.

Figure 10:
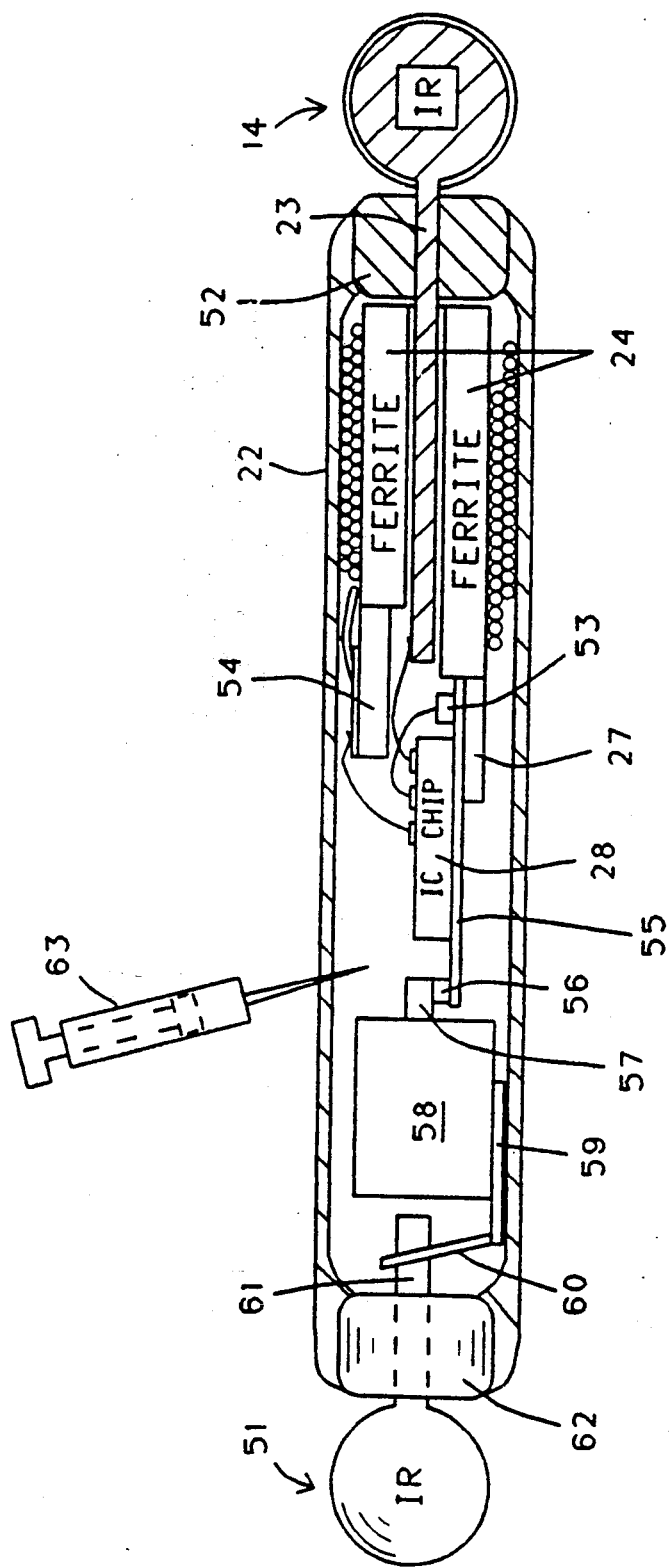
FIG. 10 illustrates a microstimulator constructed with iridium electrodes at each end and an internal capacitor.

FIG. 10 illustrates a preferred embodiment in which iridium electrodes 14 and 51 are disposed at opposing ends of the microstimulator. Iridium stem 23 extends through glass bead 52 and then through the center of ferrite 24. Diode 53 may be mounted as shown or be constructed within electronic chip 28. It has been found that ferrite shelf 27 is prone to break and therefore, if shortened, a miniature metal plate 55 may be adhered to it and provide adequate space for mounting electronic chip 28, diode 53 and shim 56. Electrolytic capacitor 58 is connected to shim 56 through electrode 57. The other electrode of capacitor 58 is its external surface, or case, which is connected to metal plate, or metallization 59 which, in turn, is connected by a wire 60 to iridium electrode stem 61 which extends through glass bead 62.

Hypodermic syringe 63 may be utilized to fill up the housing 22 with epoxy, silicon rubber or other suitable inert material which is impervious to water. Such material may be added while the internal assembly is being moved into the housing 22 or after the internal assembly is in place and iridium electrodes 14 and 51 are disposed to extend out each end of the microstimulator. The material itself, or other sealant, may seal up the hole or aperture through which the syringe enters the housing.

Inasmuch as the electronic chip 28 is light sensitive, a light barrier must be provided. Such light barrier may be a film or mask placed on the chip, an opaque or colored material used to fill the microstimulator, or a housing which is opaque or colored so as to prevent undesired light from reaching the chip 28.

Although specific embodiments and certain structural arrangements have been illustrated and described herein, it will be clear to those skilled in the art that various other modifications and embodiments may be made incorporating the spirit and scope of the underlying inventive concepts and that the same are not limited to the particular forms herein shown and described except insofar as determined by the scope of the appended claims.

We claim:

1. An implantable microstimulator substantially encapsulated within a hermetically-sealed housing which is inert to body fluids, said microstimulator being of a size approximately 2 mm in diameter and 10 mm in length and of longitudinal shape capable of implantation in the immediate vicinity of selected areas of the body by expulsion through a hypodermic needle, a first inert, metallic electrode hermetically sealed to said housing at or near one end thereof and a second inert, metallic electrode hermetically sealed to said housing at or near another end thereof, and a substantial portion of said electrodes being exposed outside said microstimulator so as to provide stimulation pulses, a coil having a multiplicity of turns of a fine, electrically-conductive wire adapted to act as the secondary of a transformer and receive a modulated, alternating magnetic field, said alternating magnetic field providing power for said microstimulator and said modulation providing control information for said microstimulator, capacitor means for storing power received from said magnetic field, electronic circuitry, means for electrically connecting said electronic circuitry in circuit with said coil, said capacitor means and said electrodes.

2. The microstimulator recited in claim 1 wherein said electrodes are both iridium and said capacitor means is in electrical circuit between one of said electrodes and said electronic circuitry.

3. The microstimulator recited in claim 2 wherein said capacitor means comprises a plurality of capacitors at least one of which is between one of said electrodes and said electronic circuitry.

4. The microstimulator recited in claim 1 wherein said coil has approximately 200 or more turns.

5. The microstimulator recited in claim 1 wherein said coil is wound on a low-loss, high permeability core.

6. The microstimulator recited in claim 5 wherein said core has a channel through which one of said electrodes extends and is electrically connected to said electronic circuitry which is disposed at or near the end of the core nearest the other electrode.

7. The microstimulator recited in claim 6 wherein said electrical conductor extending through said core is at least partially embedded in a heat-conductive material disposed within said channel in said core, thereby using said core as a heat sink for said conductor.

8. The microstimulator recited in claim 5 wherein said core has a shelf thereon and a metal plate adhered to said shelf and extending beyond the end thereof, said electronic circuitry being disposed on said metal plate.

9. The microstimulator recited in claim 1 wherein said means connecting said electronic circuitry to one of said electrodes comprises a conductive, metallized pad adhered to said shelf and wherein one of said electrodes is electrically connected to said pad, and wherein said electronic circuitry is disposed in a conductive substrate and said substrate of said electronic circuitry is disposed on said metallized pad, thereby connecting said electrode to said electronic circuitry.

10. The microstimulator recited in claim 1 wherein one or more of said electrodes is an iridium ball having an electrically-conductive stem extending into said housing and hermetically sealed with respect to said housing by fusing at or near the end of said housing, with a substantial portion of said ball exposed to provide electrical stimulation.

11. The microstimulator recited in claim 10 wherein, at least a portion of the exposed portion of said iridium ball is electrochemically-activated, forming a stable oxide coating thereon, whereby the charge-carrying capacity of said ball is substantially increased.

12. The microstimulator recited in claim 1 wherein said electrodes have stems connected thereto and each of said stems is fused to a glass bead which glass beads are, in turn, fused to said housing of said microstimulator to provide a hermetic seal.

13. The microstimulator recited in claim 1 wherein said electrodes are both iridium.

14. The microstimulator recited in claim 1 wherein one or more of said electrodes is an inert, bio-compatible metallic film adhered to said microstimulator.

15. The microstimulator recited in claim 1 wherein is included means for anchoring said microstimulator in place within the body.

16. The microstimulator recited in claim 15 wherein said means for anchoring comprises a resilient skirt having one or more arms which are adapted to be resiliently compressed against the sides of said microstimulator while it is disposed within a hypodermic needle and are adapted to spring away from the body of said microstimulator upon release of said microstimulator within the body.

17. The microstimulator recited in claim 15 wherein said means for anchoring comprises spacing the enlarged end of an electrode on the order of 0.010" from the end of said housing, wherein body tissue fills in said space.

18. The microstimulator recited in claim 1 wherein at least one of said electrodes is disposed on said housing and adapted to be substantially transparent to said varying, electromagnetic field.

19. The combination recited in claim 1 wherein at least one of said electrodes is elongated and extends away from said housing.

20. The microstimulator recited in claim 19 wherein said elongated electrode comprises hook-like means for keeping one or more of said electrode and said microstimulator in place.

21. The microstimulator recited in claim 1 wherein a plurality of elongated electrodes extend from said housing.

22. An implantable microstimulator substantially encapsulated within a hermetically-sealed housing which is inert to body fluids, said microstimulator being of a size approximately 2 mm in diameter and 10 mm in length and of a shape capable of implantation through a hypodermic needle, said microstimulator having a first electrode comprising an iridium ball having an electrically-conductive stem extending into said housing and hermetically sealed to said housing at or near one end thereof and a substantial portion of said ball being exposed outside said microstimulator, and a second electrode comprising an inert, metallic conductor comprising an electrically-conductive stem extending into said housing and hermetically sealed to said housing at or near the other end thereof, said metallic conductor having a substantial portion thereof exposed outside said microstimulator, a ferrite core having approximately 200 or more turns of a fine, electrically-conductive wire wound therearound, forming a coil, electronic circuitry disposed at or near one end of said ferrite core, means connecting said electronic circuitry electrically to said coil and said electrodes, wherein information and power may be received by said coil, inside the body, from an alternating magnetic field, modulated in accordance with information, said field being generated from outside said body, and wherein said electrodes provide electrical stimulation to the body and are adapted to be controlled by said electronic circuitry in accordance with said power and said information.

23. The microstimulator recited in claim 22, wherein said coil has approximately 250 turns of approximately 0.001" D wire.

24. The microstimulator recited in claim 22, wherein said means connecting said coil to said electronic circuitry comprises one or more metallized pads disposed on said ferrite, said coil being electrically connected to said pads and said pads being further connected to said electronic circuitry by electrical conductors.

25. The microstimulator recited in claim 24 wherein said two pads of metal are comprised of metal selected from the group comprising palladium, silver, indium, solder and mixtures thereof, and each end of said coil being electrically connected to a respective pad and a gold wire being bonded to each of said metallized pads and to a respective conductive pad on said electronic circuitry.

26. The microstimulator recited in claim 22, wherein the electrically-conductive stem of said iridium ball extends through said ferrite to said electronics circuitry.

27. The microstimulator recited in claim 22 wherein at least one of said electrodes, said core, and said coil are radially smaller than, and can pass through the inner diameter of said housing, for assembling said microstimulator.

28. The microstimulator recited in claim 22 wherein an inert gas is disposed within said microstimulator.

29. The microstimulator recited in claim 22 wherein said microstimulator is filled with a solid which is an inert material impervious to water.

30. An implantable microstimulator of a size capable of expulsion through the lumen of a hypodermic needle, said microstimulator being substantially encapsulated within a hermetically-sealed housing which is inert to body fluids, inert, metallic electrode means hermetically sealed to said housing at or near each end thereof, electronic control circuitry, capacitor means disposed between a first of said electrode means and said electronic control circuitry, induction means comprising a coil for receiving an alternating magnetic field to provide power for said microstimulator, said electronic control circuitry connected to said coil, said capacitor means and the second of said electrode means.

31. The microstimulator recited in claim 30 in which said first electrode means comprises a plurality of electrodes hermetically sealed to said housing in the other end, electronic control circuitry, said capacitor means being disposed between said plurality of electrodes and said electronic control circuitry, induction means comprising a coil for receiving an alternating magnetic field to provide power for said microstimulator, said electronic control circuitry connected to said coil, said capacitor means and said first electrode.

32. The microstimulator recited in claim 30 wherein said capacitor means comprises an individual capacitor disposed between a respective electrode and said electronic control circuitry.

33. The microstimulator recited in claim 30 in which said electronic control circuitry comprises a single microcircuit chip.

34. The microstimulator recited in claim 30 wherein said housing is comprised of one of the group consisting of glass capillary tubing, a ceramic, epoxy and silicon rubber.

35. The process for manufacturing a microstimulator comprised of a housing of a size approximately 2 mm in outer diameter and 10 mm long, two electrodes and a microminiature electronic control circuit, comprising the steps of winding a coil of approximately 200 or more turns of a fine wire, said coil having a diameter smaller than the inner diameter of said housing, so as to fit inside thereof, electrically connecting said coil and said electrodes to said electronic control circuit, inserting said coil, said electrodes, and said electronic control circuit within said housing, disposing one of said electrodes in each end of said housing, with a substantial portion of each said electrode exposed outside said housing, and hermetically sealing said electrodes to said housing.

36. The process recited in claim 35 wherein the exposed portions of said electrodes are approximately 1 to 1.5 mm in length and width and said electrodes are hermetically sealed with respect to said housing by means of heat fusing.

37. The process recited in claim 36 wherein at least one of said electrodes is iridium and after said fusing, said iridium electrode is activated.

38. The process recited in claim 36 wherein one of said electrodes is tantalum and after said fusing, said tantalum electrode is anodized.

39. The process recited in claim 35 wherein at least one of said electrodes is hermetically sealed with respect to said housing by at least a portion of said electrode being fused to a glass bead and wherein said glass bead is fused to said housing.

40. The process recited in claim 35 wherein one or more of said electrodes is hermetically sealed with respect to said housing by being fused thereto, the fusing of one or more of said electrodes also providing the necessary heat to melt a connecting flux which makes an electrical connection to one or more electrical conductors within said housing.

41. The process recited in claim 35 wherein said coil is wound around a low-loss, high-permeability core formed to provide a shelf upon which said electronic control circuit is mounted.

42. The process recited in claim 41 wherein said core further provides the base upon which a plurality of metal pads are disposed for making electrical connections within said microstimulator.

43. The process for manufacturing a microstimulator comprised of a housing of a size approximately 2 mm in outer diameter and 10 mm long, two electrodes each having an electrically-conductive stem, the process comprising the steps of winding a coil of approximately 200 or more turns of a fine wire, connecting both ends of said coil to provide input to an electronic control circuit, said coil, said electronic control circuit and at least one of said electrodes all having a diameter less than the inner diameter of said housing, disposing an electrode at each end of said coil and electronic control circuit, electrically connecting said electrodes to receive the output of said electronic control circuitry and then inserting said coil, electronic control circuit and electrodes in said housing, and hermetically sealing said electrodes to said housing with a substantial portion of each said electrode exposed outside said housing.

44. The process recited in claim 43 in which said coil is wound around a low-loss, high permeability core having a shelf for carrying said electronic control circuitry and another shelf carrying metallized pads for making electrical connection to said coil, and wherein said core has a channel therethrough through which one of said electrically-conductive stems extends.

45. The process recited in claim 43, wherein is included a low-loss, high-permeability core constructed in two, half-cylindrical parts, one part being a lower part and forming a shelf on which said electronic circuitry is disposed, assembling said microstimulator electrodes and electronic circuitry on the lower part, subsequent placement of the other part on said lower part, winding of said coil on said two parts and completion of the connection of said coil to said electronic circuitry.

* * * * *